United States Patent [19]

Allen et al.

[11] Patent Number: 4,898,037
[45] Date of Patent: Feb. 6, 1990

[54] METHOD AND APPARATUS FOR DETERMINING THE PROPENSITY OF A PAPER OR BOARD TO DUST

[75] Inventors: Roger A. Allen, Great Missenden; Geoffrey Youd, High Wycombe, both of United Kingdom

[73] Assignee: The Wiggins Teape Group Limited, Basingstoke, England

[21] Appl. No.: 221,551

[22] Filed: Jul. 20, 1988

[30] Foreign Application Priority Data

Jul. 20, 1987 [GB] United Kingdom ............... 87 17118

[51] Int. Cl.$^4$ .................................... G01N 33/34
[52] U.S. Cl. ..................................... 73/866; 73/104; 73/159; 356/429; 356/448
[58] Field of Search ............... 73/866, 159, 104; 356/448, 445, 429, 446

[56] References Cited

U.S. PATENT DOCUMENTS

| | | | |
|---|---|---|---|
| 2,236,373 | 3/1941 | Kowalski | 73/104 X |
| 2,324,126 | 7/1943 | Anway | 73/159 |
| 3,526,461 | 9/1970 | Lindahl et al. | 356/338X |
| 3,818,223 | 6/1974 | Gibson et al. | 356/448 X |
| 4,084,433 | 4/1978 | Naarding | 73/159 |
| 4,437,333 | 3/1984 | Hands | 73/159 X |
| 4,505,159 | 3/1985 | Entwistle | 73/104 X |
| 4,513,613 | 4/1985 | Darvez-Bornoz et al. | 73/159 |
| 4,558,590 | 12/1985 | Desai et al. | 73/104 |
| 4,568,835 | 2/1986 | Imamura et al. | 356/446 X |
| 4,793,710 | 12/1988 | Sapko et al. | 356/446 |
| 4,799,799 | 1/1989 | Sapko et al. | 356/446 |

FOREIGN PATENT DOCUMENTS

| | | |
|---|---|---|
| 1026993 | 3/1958 | Fed. Rep. of Germany ........ 73/159 |
| 1063406 | 8/1959 | Fed. Rep. of Germany ........ 73/159 |
| 48389 | 4/1977 | Japan . |
| 184953 | 11/1982 | Japan . |
| 1280491 | 12/1986 | U.S.S.R. . |

*Primary Examiner*—Tom Noland
*Attorney, Agent, or Firm*—Burns, Doane, Swecker & Mathis

[57] ABSTRACT

Disclosed is a method of testing the propensity of a paper or board to dust. The method is one which includes pressing a reference surface to the surface to be tested at a predetermined pressure. The dust adhering to the reference surface is then measured such that an indicative reading is obtained.

16 Claims, 14 Drawing Sheets

METHOD AND APPARATUS FOR DETERMINING THE PROPENSITY OF A PAPER OR BOARD TO DUST

BACKGROUND OF THE INVENTION

This invention relates to a method and apparatus for determining the propensity of a paper or board to dust.

Papers and boards are susceptible to the release of debris, for example fibers, particles of coating and fillers (referred to herein as dust) from their surfaces during printing processes. If the quantity of dust is excessive, it tends to contaminate printing blankets so that the quality of the print is affected. It is therefore advantageous to be able to simulate the printing process and ascertain whether a particular paper or board will shed so much dust that it is unacceptable. A number of techniques can be employed in paper making to assist in retaining the filler in the paper, but it is essential to be able to determine the effectiveness of these in preventing contamination of the printing machine. The present invention is directed to a method and apparatus for carrying out such tests.

SUMMARY OF THE INVENTION

According to the present invention a method of testing the propensity of a paper or board to dust includes pressing a reference surface to the surface to be tested at a predetermined pressure and measuring the dust adhering to the reference surface to obtain an indicative reading.

Preferably the scattered reflectance of the reference surface is measured.

The method can include measuring the scattered reflectance of the reference surface before pressing said surface to the surface to be tested and obtaining an indicative reading by comparing the two measurements.

The invention also includes apparatus for determining the propensity of a paper or board to dust which comprises means for pressing a reference surface to the surface to be tested at a predetermined pressure and means for obtaining an indicative reading from the dust adhering to the reference surface.

Thus, the means for obtaining an indicative reading may comprise means for measuring the reflectance of the reference surface.

The apparatus can include means for measuring the scattered reflectance of the reference surface before pressing it to the surface to be tested, and means for comparing the measurement obtained with the measurement obtained by pressing it to the surface to be tested to provide an indicative reading.

In one form of the apparatus according to the invention the reference surface can be substantially cylindrical and control means can be provided to cause it to move over the surface to be measured for a predetermined distance, for example one complete revolution or less.

With this arrangement the cylindrical surface can be arranged to press against a feed cylinder to form a nip and feed means can be provided to guide the paper or board to be measured between the cylinders.

The control means can also include means for sensing paper or board in the feed means, to activate the cylinders, and to stop them after a predetermined distance of movement.

The reference surface cylinder can be arranged to contact a continuous web of paper for a predetermined distance and to then disengage to an inoperative position.

If desired the scattered reflectance of the reference surface can be measured simultaneously with the passage of the surface of the material being measured.

BRIEF DESCRIPTION OF THE DRAWINGS

The invention can be performed in many ways and various embodiments will now be described by way of example and with reference to the accompanying drawings in which.

DETAILED DESCRIPTION OF THE PREFERRED EMBODIMENTS

Figure 1:
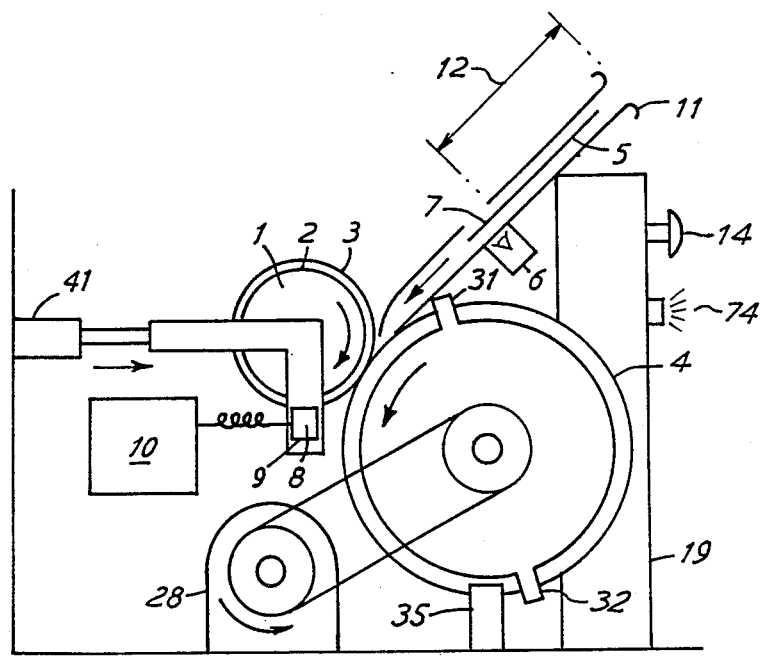
FIG. 1 is a diagrammatic illustration of the apparatus.

As shown in FIG. 1 apparatus for determining the quantity of dust, for example in the form of debris formed by fibres, coating, fillers and other materials which are released from the surface of paper and board, during a printing process, comprises a cylindrical roll 1 provided with an elastomeric covering 2 which provides a reference surface 3. Located beneath the roll 1 is a metal feed cylinder 4. An electrical drive motor 28 is used for rotating the roll 4 at a predetermined desired speed so that when a paper strip 5 to be tested is sensed by a detector 6 the roll 1 is brought into contact with cylinder 4 and the paper 5 is passed through the nip between them at a predetermined pressure. When one revolution of the roll 1 has been completed the drive from motor 28 is disconnected and the nip opens.

Dust and debris released from the surface 7 of the paper 5 are transferred to the reference surface 3 of the roll 1 and the amount of dust is represented by the change in reflectance of the reference surface 3. This is measured by a light source 8 and a detector 9 with its associated electronics 10 which is shown in more detail in FIGS. 9 and 10. The reference surface is usually coloured black and will change to a greyish tone with a build up of dust.

An initial measurement of the scattered reflectivity of the clean reference surface 3 is taken. It may then be necessary to pass a number of strips of paper 5 between the roll 1 and cylinder 4 before a second reading is taken for comparison with the first but this will depend upon the measuring standards which are set. For example, the reflectance of the roll could be measured a second time after, say, a hundred strips have passed through, and the change in reflectance plotted (either manually or automatically) over these hundred strips. The more dust that is transferred to the surface 3 for a given number of strips the worse the paper can be expected to perform in the printing process in that more dust will be transferred to the printing blanket, thus lowering the print quality.

A mechanism is provided (to be described) which enables the roll 1 and cylinder 4 to be brought together and held in that position for one revolution of the roll 1 and for the nip then to open ready for the next strip of paper. This not only ensures that a precise length of paper is tested but also obviates the possibility of dust being transferred back to the feed cylinder 4 as will happen if the reference surface 3 continues to revolve in contact with the cylinder 4 after the strip of paper has passed the nip.

In more detail, FIG. 1 shows operation of the control apparatus for the roll 1 and cylinder 4. Paper strip 5 is delivered down a guide chute 11. If the paper is arranged, for example, to be a strip of A4 length the dimension 12 between the entrance to the chute and the detector 6 is arranged to be of a greater length. The detector 6 in this case can be a diffuse reflective photohead which will immediately be activated as the paper passes it. Activation of the detector causes operation of the feed cylinder 4 and in the construction being described also causes reference surface 3 to be pivoted, by means of a pneumatic ram 41, into contact with the feed cylinder 4. The cylinder 4 has twice the circumference of roll 1, and the feed cylinder 4 carries two marker fingers 31 and 32 which serve as roll stop reference points activating a proximity sensor switch 35. When the roll 1 has completed one revolution, the marker 31 or 32 passes the proximity sensor switch 35. This causes the drive to the feed cylinder 4 to be disconnected and the pneumatic ram 41 to operated so as to draw reference surface 3 away from feed cylinder 4, thus ensuring that only the dust from a predetermined length of the surface of paper 5 has been transferred to the reference surface 3.

Figure 5:
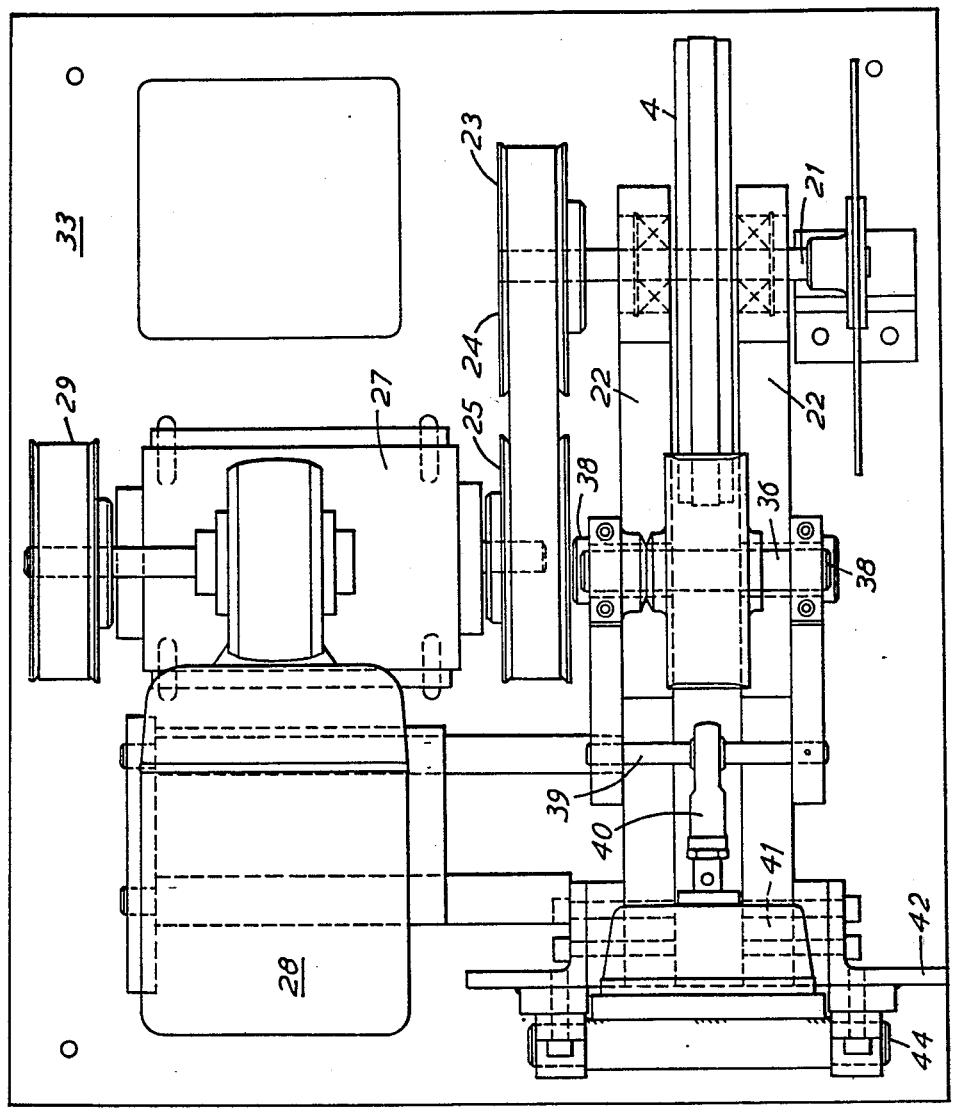
FIG. 5 is a plan view of the apparatus shown in FIGS. 3 and 4.

Guide means are provided which include a deflector for guiding the paper away from the reference surface 3 after contact therewith and are shown in FIG. 5 to be described hereunder.

Figure 2:
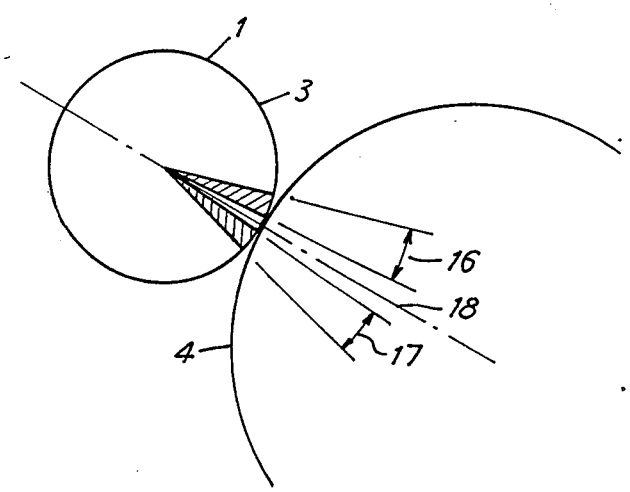
FIG. 2 is a diagram indicating part of the manner of operation of the apparatus shown in FIG. 1.
Figure 3:
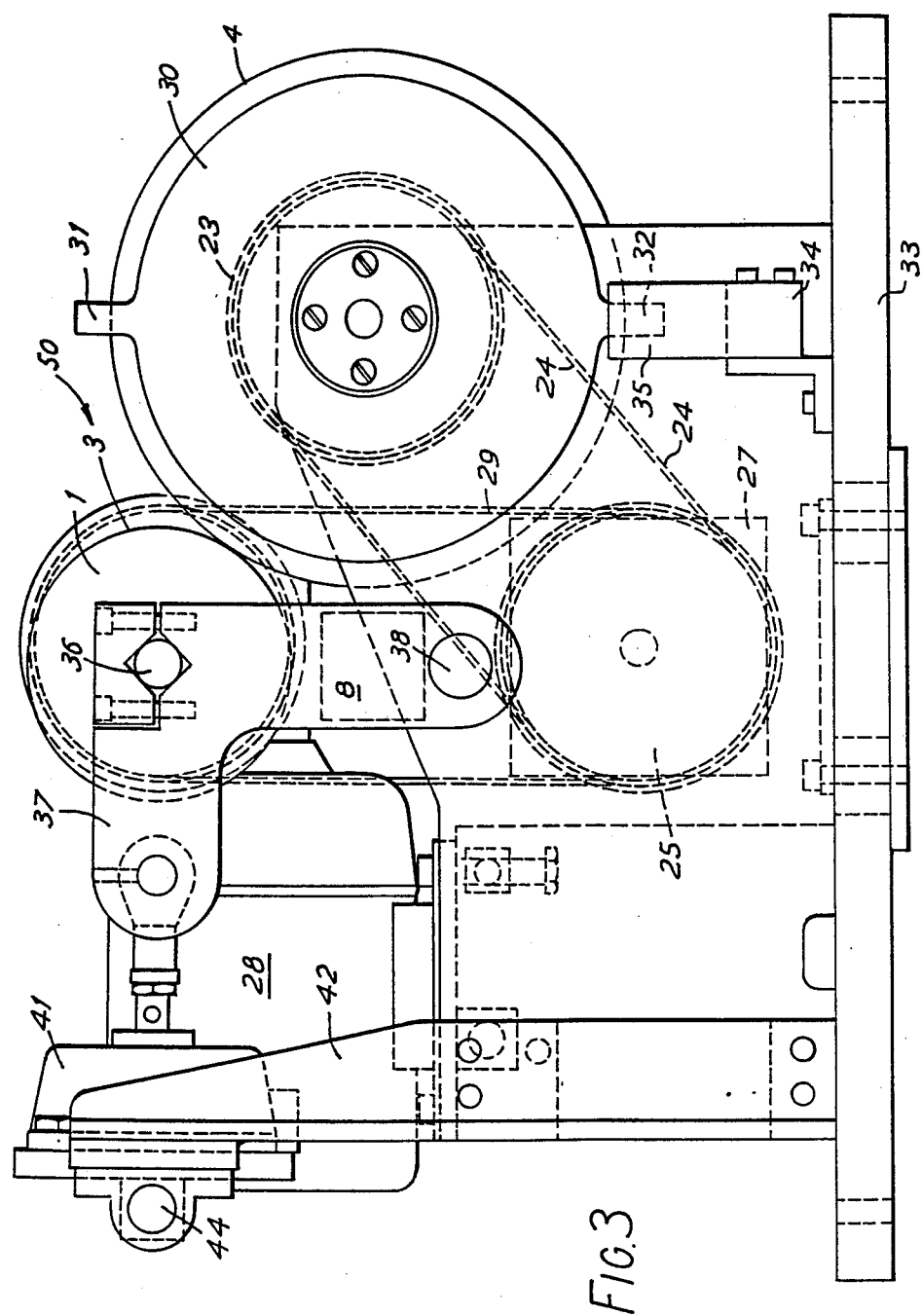
FIG. 3 is a side elevation of a practical construction of part of the apparatus.
Figure 4:
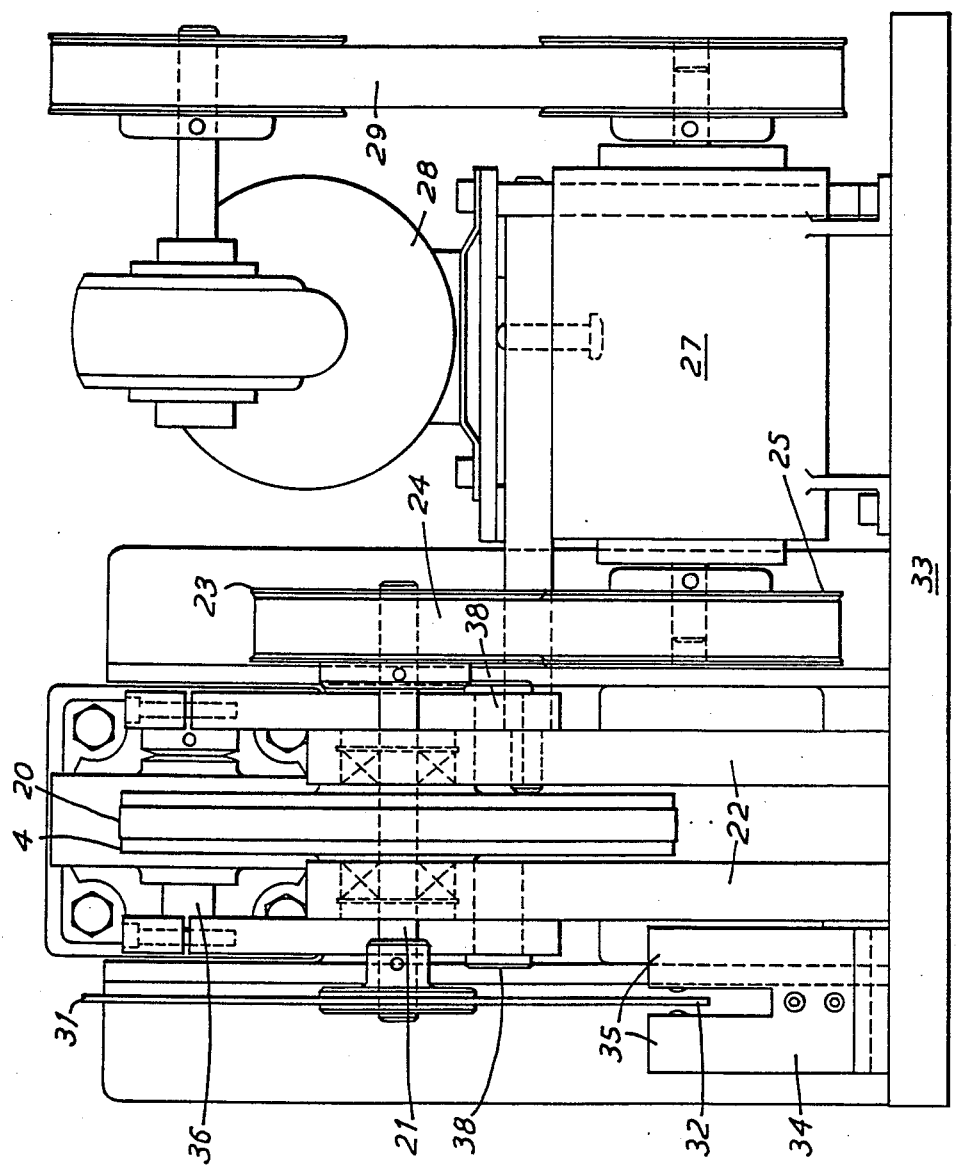
FIG. 4 is an end view of the apparatus shown in FIG. 3.

FIG. 2 illustrates diagrammatically the operating zones which are effective on the roll 1. An acceleration surface sector equal to approximately 7 degrees is indicated by reference numeral 16 and a similar braking area is indicated by reference numeral 17. There is a small area in between these which indicates the start/stop contact zone and is indicated by reference numeral 18.

The roll 1 is arranged to stop in the same position for each revolution, the only variables being any voltage and frequency fluctuation in the electrical supply operating the drive.

A control cabinet 19 is provided to house all the relays, controllers, timers and other mechanism which will be described later. The only mechanism requiring actuation by the operator is a start button 14.

More details of the construction of the apparatus are shown in FIGS. 3, 4, 5, 9, 10, 11 and 12. The feed cylinder 4 is provided with a raised land 20 on its circumference and is carried on a spindle 21 mounted on supports 22. One end of the spindle 21 carries a driven pulley 23 which is driven by a toothed belt 24 from a drive pulley 25 mounted on the operating spindle 26 of a combined clutch and brake 27. The clutch and brake 27 is driven at a constant speed by an electric motor 28 through a toothed belt 29.

The end of the spindle 21 remote from the driven pulley 23 carries a timing wheel 30 having projecting marker fingers 31 and 32 at diametrically opposed positions.

The supports 22 are carried on a base 33 on which is mounted a proximity sensor switch 35 which is most clearly shown in FIG. 5.

The reference roll 1 bearing its reference surface 3 is mounted to freely revolve on a spindle 36 carried on bell-crank shaped arms 37. The lower ends of the arms 37 are carried on pivots 38 and the other ends of the arms are connected by a cross-member 39 to which is pivotally secured an adjustable ram arm 40. The ram arm 40 is connected to a pneumatic ram 41 carried on a mounting indicated by reference numeral 42 and which is secured to the base 33. The ram is pivoted at 44 to accommodate the movement of the bell-crank arms 37.

The direction of feed from the feed chute (not shown in FIGS. 3, 4 and 5) is indicated by arrow 50.

Figure 6:
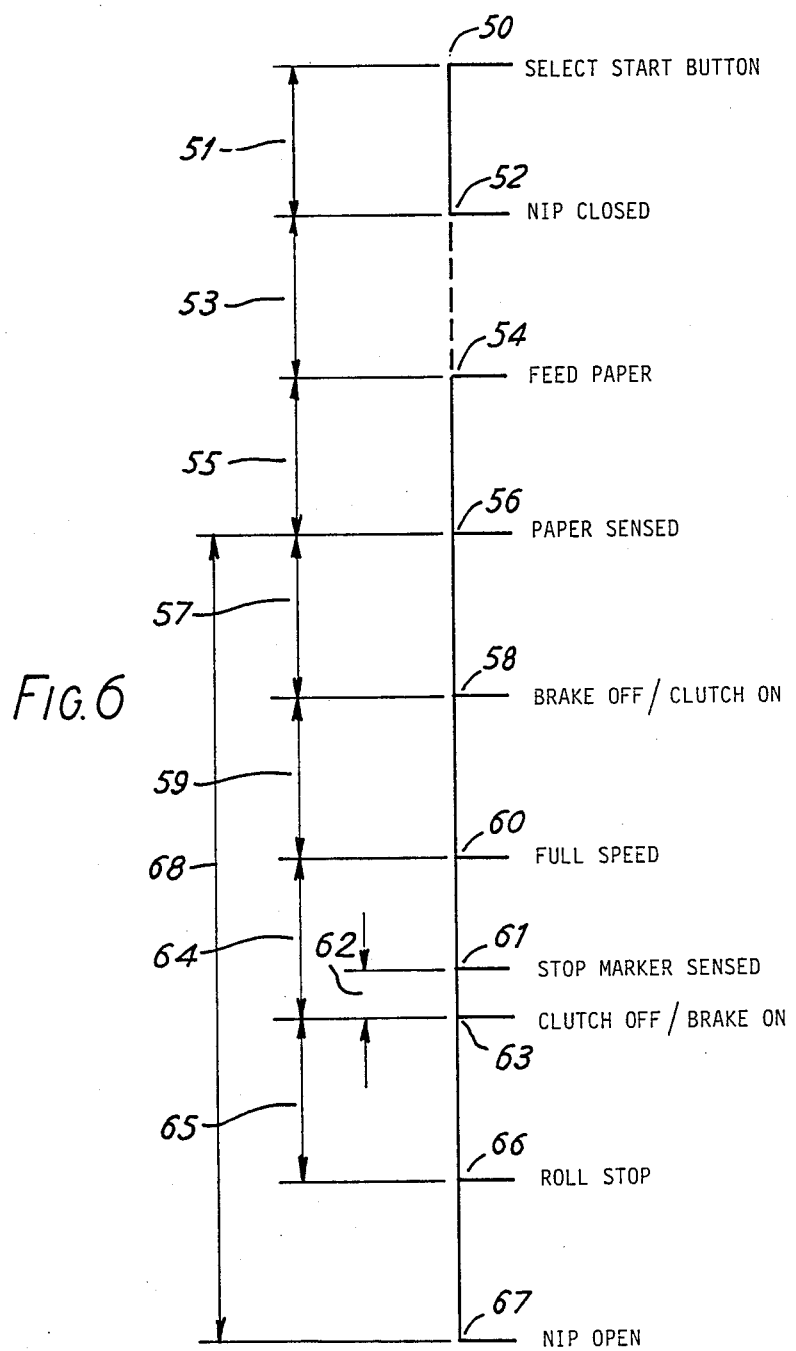
FIG. 6 is a sequence diagram indicating the method of operating the apparatus.

FIG. 6 shows the sequence of operation of the various parts. With the electric motor 28 running there is a constant drive into the clutch and brake 27. In order to operate the apparatus the start button 14 is operated this causes the nip between the roll 1 and cylinder 4 to close. In FIG. 6 the time of pressing the operating button 14 is indicated by reference numeral 50. Reference numeral 52 indicates the point at which the nip closes. The arrow 51 indicates the time period between the operation of the button and nip closure. Time period 53 is dependent upon the speed at which the operator feeds the paper 5 to be tested as indicated by reference numeral 54. The time period 55, which is approximately 1 second, indicates the period after which the paper is sensed by the detecting means 6 as indicated by reference numeral 56. After a further time period 57 of 1 second, the electrical control system simultaneously releases the brake and engages the clutch 27 at the stage indicated by point 58. A further time period 59 of 20 milliseconds elapses for the cylinder 4 to reach full speed. This is referred to as the acceleration period, the end of which is indicated by reference numeral 60. At this stage the cylinder 4 will be rotating at full speed and pressed against the reference surface 3 with the paper for testing nipped between them, the nip having been closed by operation of the ram 41.

The cylinder 4 continues to rotate until the marker finger 31 or 32 reaches the proximity sensor switch 35 where it is sensed, this point being indicated by reference numeral 61 in FIG. 6. A time period of 12 milliseconds indicated by reference numeral 62, elapses before the clutch is released and the brake simultaneously applied at point 63. The time period from the full speed position 60 to the clutch off/brake on position 63 is 89 milliseconds and is indicated by reference numeral 64. A deceleration braking period of 20 milliseconds, indicated by reference numeral 65, elapses before the roll stop position 66 is reached. This roll stop position will coincide with one complete revolution of the roll 1. The electrical control system now causes the nip to open by withdrawing the roll 1 and this position is indicated by reference numeral 67. The total time period between the paper being sensed at 56 and the nip opening at 67 is 2 seconds and is indicated by reference numeral 68. The apparatus is now in its original position prior to operation of the start button 14.

Figure 7:
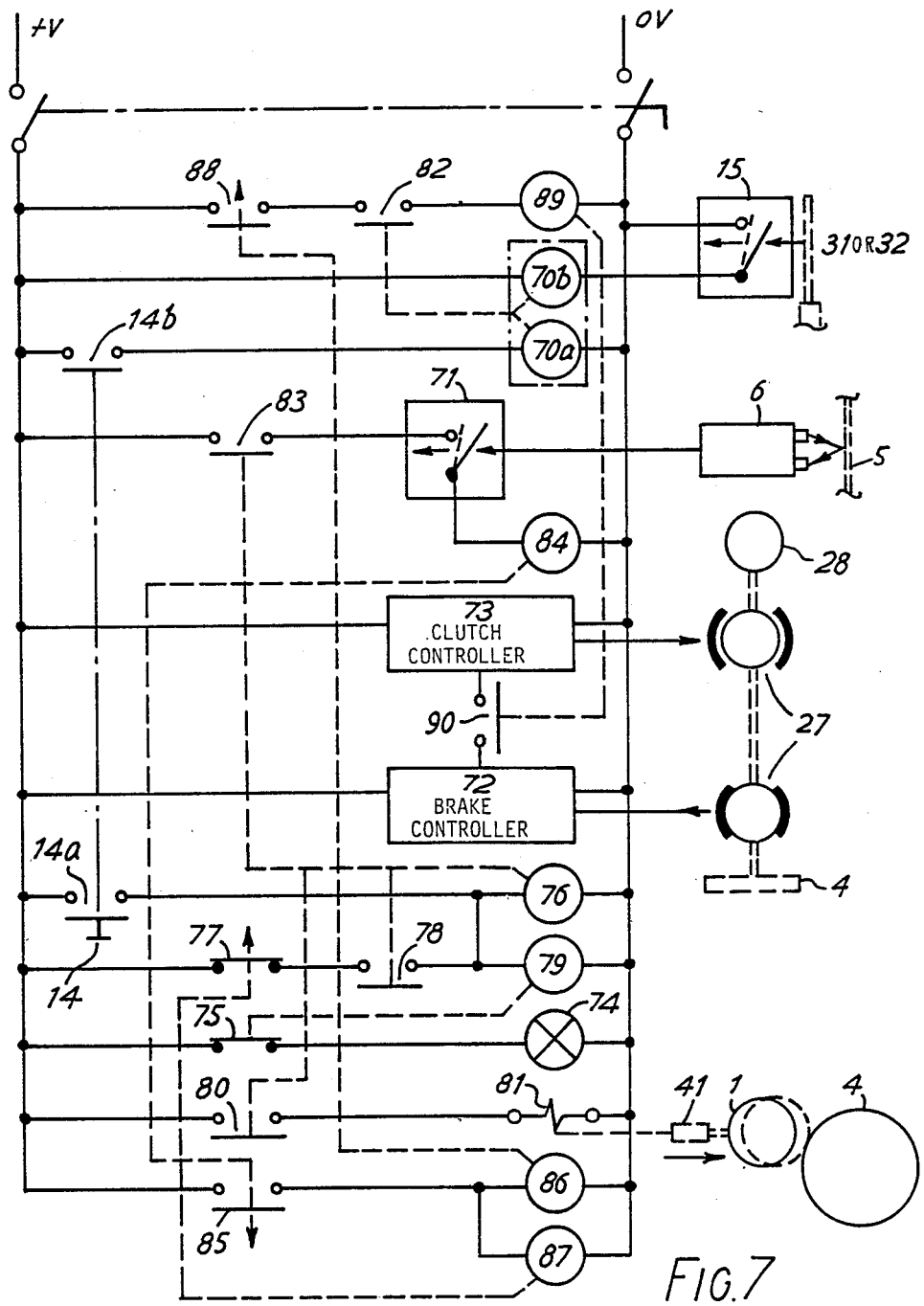
FIG. 7 is a diagrammatic electrical control diagram for the apparatus.

A diagrammatic electrical circuit for controlling and operating the various parts is shown in FIG. 7, the circuit being shown in a de-energised state.

A typical control sequence description is as follows:

At the sequence start a closed contact 75 of sequence start relay 79 illuminates the indicator lamp 74 as shown in FIG. 1 and FIG. 7. Nip closure is now selected by pressing the start button 14 (see also FIG. 1). A fleeting contact 4a of the start button 14 simultaneously energises the sequence start relay coil 79 and the nip close relay coil 76, which are held in by a closing contact 78 of the nip close relay 76 and a closed contact 77 of the sequence finish timer relay 87. The sequence start relay 79 contact 75 opens, extinguishing the sequence start lamp 74. At the same time the nip close relay 76 contact 80 closes energizing the roll nip solenoid 81, actuating the pneumatic ram 41, thus engaging the reference roll 1 to the feed cylinder 4 and the nip close relay 76 contact 83 closes enabling the paper sensor controller 71. Also on selection of the start button 14 a second fleeting contact 14b pulses the roll stop latching relay reset coil 70a closing its contact 82.

The paper 5 is now inserted into the chute 11 and is detected by the sensor 6 which energizes the paper sensor controller output relay 71 which via the aforementioned closed contact 83 energizes the paper detect timer relay coil 84. Its timed contact 85 closes instantaneously thus energizing the roll run timer relay coil 86 and the sequence finish timer relay coil 87.

After a time delay of one second, to enable the paper to float into the nip, the roll run timer relay 86 timed contact 88 closes and via the aforementioned closed roll stop relay contact 82 energizes the roll run relay coil 89. Its contact 90 closes between the fast operation brake and clutch units 72 and 73 to release the brake and engage the clutch 27.

The reference roll 1 will now rotate until one of the marker fingers 31 or 32 on the feed cylinder 4 is sensed by the proximity switch 15, closing its internal contact, thus pulsing the roll stop latching relay set coil 70b opening its contact 82. This de-energizes the roll run relay coil 89 whose contact 90 opens between the fast operation brake and clutch units 72 and 73 to release the clutch and engage the brake 27, thus stopping the reference roll 1 after one revolution and the feed cylinder 4 after one half revolution.

Due to the paper 5 being transported away from the sensor 6 by the rotation of the feed cylinder 4, the paper sensor controller output relay 71 is de-energized. This de-energises the paper detect timer relay coil 84 whose timed contact 85 after a delay of three seconds opens de-energising the roll run timer relay coil 86 and the sequence finish timer relay coil 87. The roll run timer relay 86 timed contact 88 opens instantaneously, inhibiting the roll run relay 89. After a time delay of two seconds the sequence finish timer relay 87 timed contact 77 opens, thus de-energising the nip close relay coil 76 and the sequence start relay coil 79. The nip close relay 76 contacts 83, 78 and 80 open instantaneously—contact 83 inhibiting the paper sensor controller 71, contact 78 cancelling the hold in function for the nip close relay coil 76 plus the sequence start relay coil 79 and contact 80 de-energising the roll nip solenoid 81 thus actuating the pneumatic ram 41, dis-engaging the reference roll 1 from the feed cylinder 4. Simultaneously the sequence start relay 79 contact 75 closes illuminating the sequence start lamp 74.

The apparatus is now ready to start another sequence if required.

The elastomeric covered roll 1 which provides the reference surface 3 is arranged to be removable so that it can be replaced for each test run. It can be of any convenient color but it has been found that black provides the best contrast when measuring reflectance.

Any elastomeric covering can be used, but neoprene and nitrile rubbers have been found to be particularly suitable with a hardness in the range 40-80 shore A.

In the above construction the reference surface on the roll 1 is arranged to rotate for one complete revolution but if desired it could be arranged to rotate for a number of revolutions to cover a predetermined length of paper or board to be tested and rather than provide a series of short strips of paper for testing a long continuous strip taken across the width of the paper sheet concerned could be utilized.

It will be apparent that there are various ways of operating the equipment to provide an indicative reading.

Figure 8:
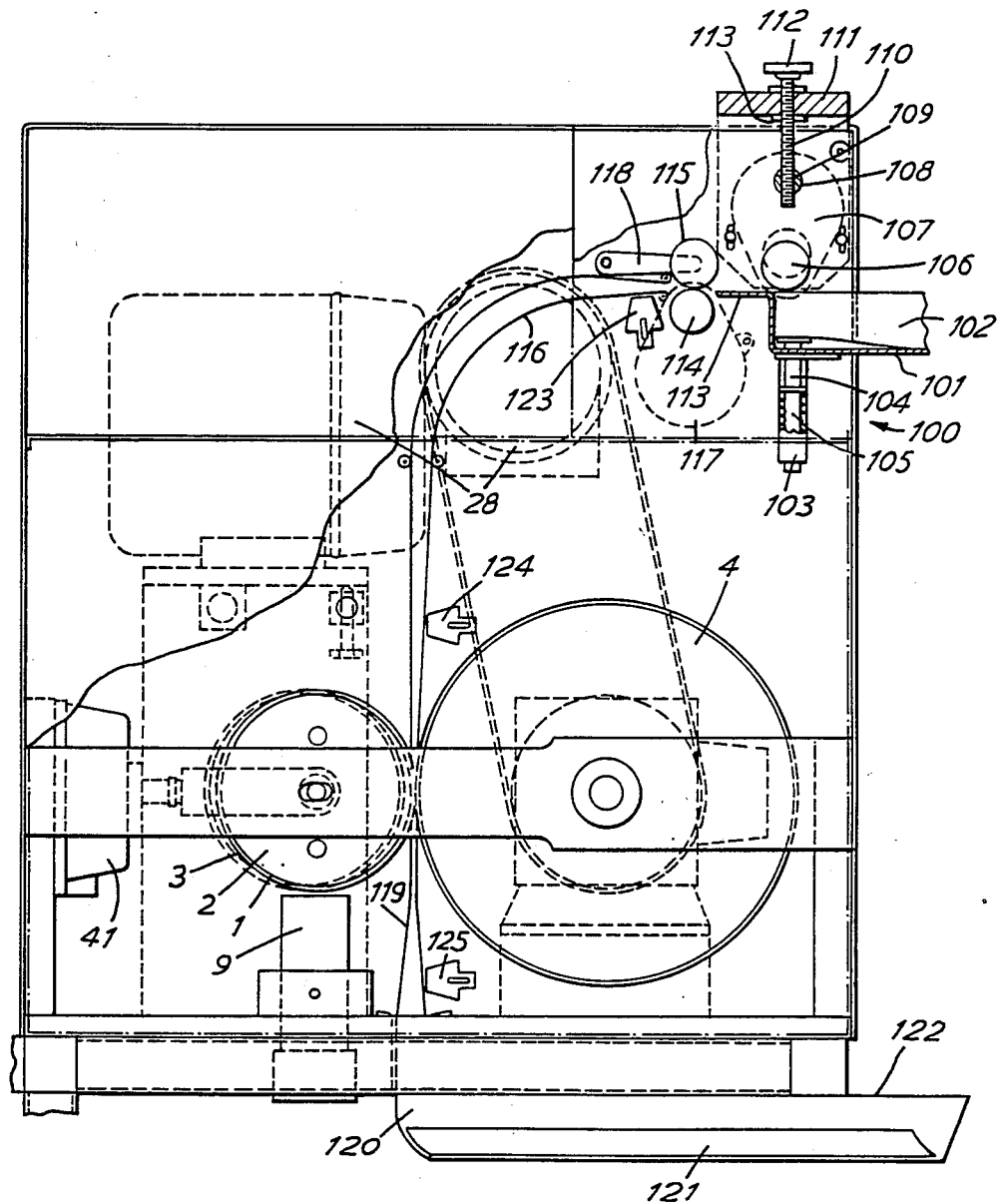
FIG. 8 shows an automatic strip feed mechanism for use as an alternative to the chute 11 shown in FIG. 1 when large numbers of strips are to be tested.

Referring now to FIG. 8, this shown an automatic strip feed mechanism 100, incorporated in an apparatus according to the invention which will in itself not be further described, similar parts being given the same reference numerals.

The automatic strip feed mechanism 100 comprises a strip feeder tray 101 which is capable of accommodating a stack 102 of paper strips to be tested. Typically, the tray 101 would be capable of accommodating 100 strips. A cylinder 103 is mounted beneath the tray at the front end thereof and accommodates a piston 104 biassed upwardly through the floor of the tray by a coil spring 105 so as to bear upwardly against the leading end of the strip stack 102.

A feed roll 106 is mounted for rotation above the piston 104 in bearings (not shown) carried in trunnions 107. The trunions 107 are connected by a tie bar 108 in which a threaded vertical bore 109 is formed. A threaded adjustment rod 110 is engaged in the bore 109 and extends upwardly through a casing 111 to terminate in a knurled adjustment knob 112. Collars 113 are secured to the rod 110 above and below the casing 111 to prevent vertical movement of the rod.

By rotating the adjustment rod 110 with the knob 112, the trunnions 107 and roller 106 can be positioned so as to compress the stack 102 against the piston 104 against the resistance of the spring 105 and so that the uppermost strip in the stack is in line with the top edge of the tray 101. Rotation of the roll 106 will then feed the uppermost strip along a support plate 113 forming an extension of the tray 101.

Two rolls 114 and 115 form a forwarding nip aligned with the support plate 113 and with the mouth of a chute 116 extending from the nip. The roll 114 is mounted in bearings (not shown) carried in two fixed trunnions 117. The roll 115 is carried in bearings (not shown) supported between two pivoted arms 118 which are spring biased so as to drive the roll 115 into engagement with the roll 114.

The strip feed roll 106 and the nip roll 114 are each separately driven by separately controllable motors (not shown).

The chute 116 extends downwardly for guiding individual strips in sequence into the nip between the rollers 1 and 4. A collector chute 119 receives strips discharged from the nip between rolls 1 and 4 and feeds them into a collector tray 120 to form a stack 121 of tested strips. The stack 121 can be removed from the tray 120 through an opening 122.

A photoelectric sensor 123 is positioned at the beginning of the chute 116 so as to detect the presence or absence of a strip at that point. Second and third sensors 124 and 125 are located respectively towards the end of the chute 116 and the collector chute 119.

In operation, the nip between the rolls 1 and 4 is first closed as hereinbefore described. This causes the motors driving the strip feed roll 106 and the nip roll 114 to start. The strip feed roll 106 feeds the top strip from the stack 102 across the plate 113 into the forwarding nip formed by the rolls 114 and 115. The rolls 114 and 115 feed the strip into the chute 116, where the leading end is detected by the sensor 123. This trips a relay controlling the drive motor for roll 106, which stops, but permits roll 106 to free-wheel. The sensor 123 then detects the passage of the trailing end of the strip and triggers the relay controlling the motor which drives roll 114. This motor then stops.

If the foregoing sequence is followed without a stack of strips 102 being present in the tray 101, the sequence is still followed until, after a time limit, the sensor 123 fails to detect the presence of a strip. In these circumstances, the motors driving rolls 106 and 114 are stopped.

A strip feed down the chute 116 as described above will fall past the detector 124 into the closed nip formed between the rolls 1 and 4. After a short time delay to ensure that the strip is correctly positioned, the drive to the roll is started so as to pass the strip through the nip for detecting scattered reflectivity of the surface dust on the sheet. The pick up roll 4 rotates one revolution whilst the dust adherent to the roll 1 is measured by the measuring head 9.

The sensor 125 is spaced from the nip between the rolls 1 and 4 by distance corresponding to the length of the strip. As the leading edge of a strip passes the sensor 125, the nip is caused to open so that the strip drops onto the stack 121 in the collector tray. As the trailing edge of the strip passes the sensor 125, the nip between the rolls 1 and 4 is again caused to close, whilst, simultaneously, the rolls 106 and 114 are started to commence the feeding of the next strip for testing. If, after a time limit, the sensor 125 does not detect the presence of a strip, the nip between the rolls 1 and 4 is opened and the tester stopped.

Further details of parts common to the construction shown above are illustrated in FIGS. 9, 10, 11 and 12.

Figure 9:
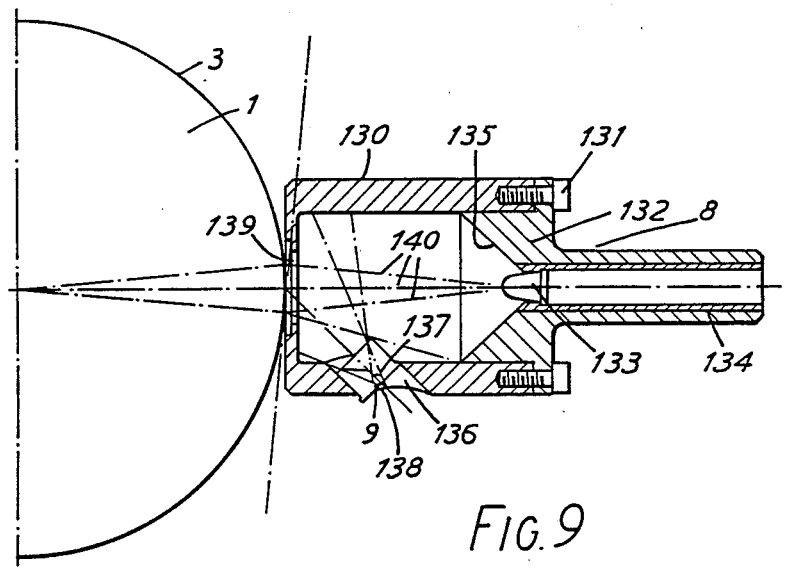
FIG. 9 is a cross-sectional side view of the light source and detector.
Figure 10:
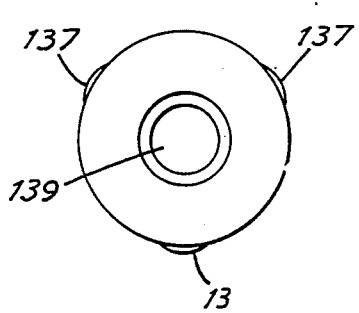
FIG. 10 is an end elevation of the device shown in FIG. 9.

The light source 8 and detector 9 are shown in more detail in FIGS. 9 and 10 and comprise a casing 130 secured by set screws 131 to a cylindrical mounting 132. The mounting 132 has a conical surface 135 at the centre of which an LED light source 133 is located in a bore 134. Three angled openings 136 are equally spaced around the side walls of the casing 130. A mounting 137, carrying a photoelectric cell 138, is located in each opening 36.

The outer end of the casing 130 is provided with a stepped opening 139 to enable the device to be located closely adjacent to the reference surface 3 of the cylindrical roll 1, as is most clearly shown in FIG. 9.

Light rays from the LED light source 133 are focussed narrowly to strike the surface 3 of the roll 1 over the area of the opening 139 as indicated by broken lines 140. The scattered reflectivity of the illuminated area is measured by the cells 138, which are positioned so as to avoid sensing direct specular reflectance from the LED light source.

The included angle of the conical surface 135 is 85 degrees and the angle between the longitudinal axis of the bore 134 and the axis of the photoelectric cells 138 is 45 degrees.

Figure 11:
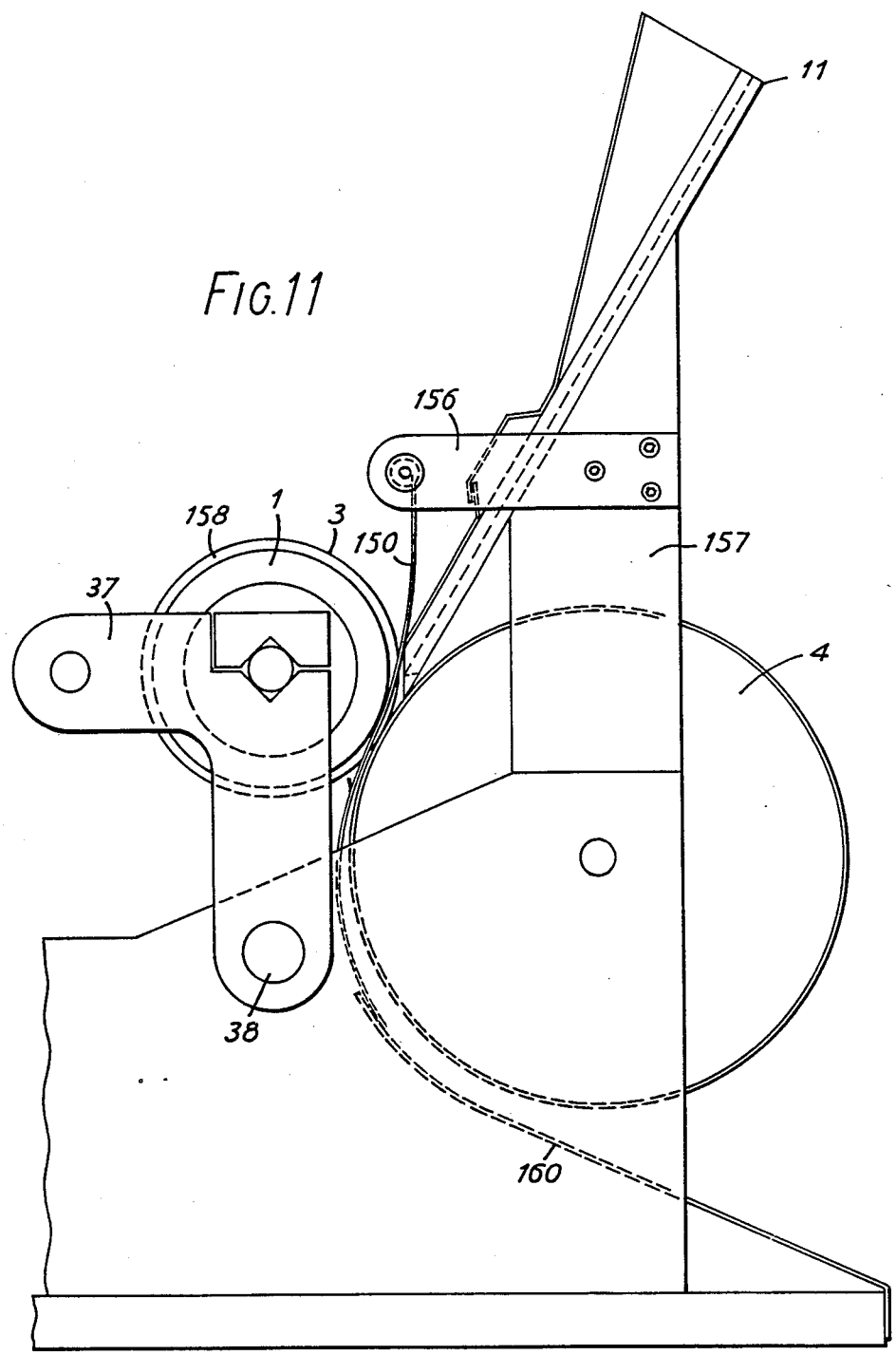
FIG. 11 is a side elevation showing paper guide means.
Figure 12:
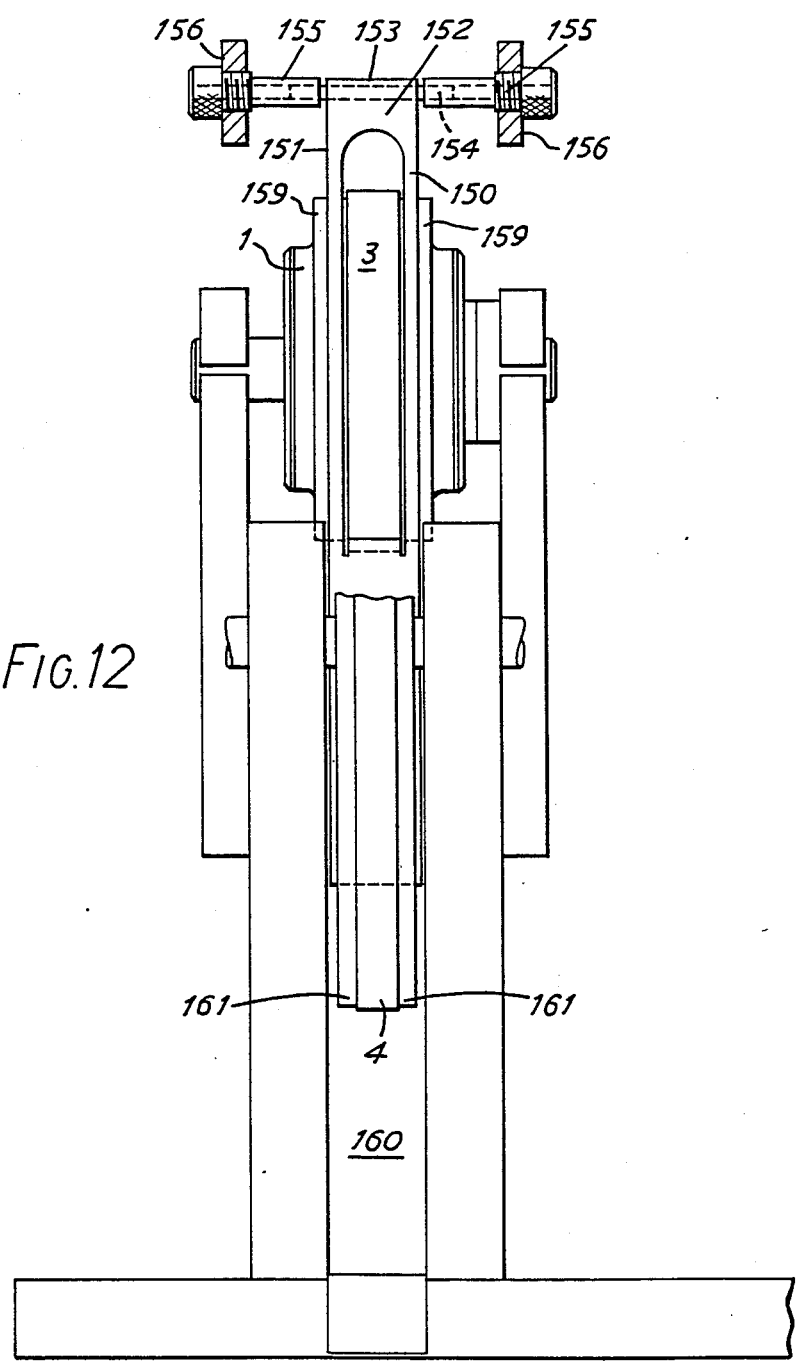
FIG. 12 is an end view of the guide means shown in FIG. 11.

FIGS. 11 and 12 show the construction of guide means to prevent the paper strips from adhering to the reference surface 3. Similar reference numerals are used to indicate similar parts as in the preceding Figures. The guide means comprises a pair of spaced apart guide strips 150, 151 which are joined at their upper end by a connecting portion 152. This portion is formed as a sleeve 153 engaging around a threaded pin 154. The ends of the pin 154 engage with knurled tubular nuts 155 which extend through brackets 156 secured to the frame 157 of the device.

As will be seen from FIG. 12 the outer periphery of the roll 1 has a raised circumferential face 158 on which the reference surface 3 is carried, and adjacent cut back portions indicated by reference numerals 159 as is most clearly shown in FIG. 12.

The strips 150, 151 are curved, as shown in FIG. 12 so that they extend downwardly from the pin 154 and closely adjacent to or in contact with the cut back portions 159 on the wheel 1. They then curve around the roll 4 to an inclined chute 160. As will be seen from FIG. 12 the surface of the drive roll 4 also has cut back portions 161 so that the configuration is similar to that of the roll 1.

In operation paper strips inserted into the chute 11 will pass down the chute and through the nip between the two rolls. The paper strip is prevented from adhering to the reference surface 3 by the strips 150, 151, which guide it around the drive roll 4 and onto the chute 160.

Figure 13:
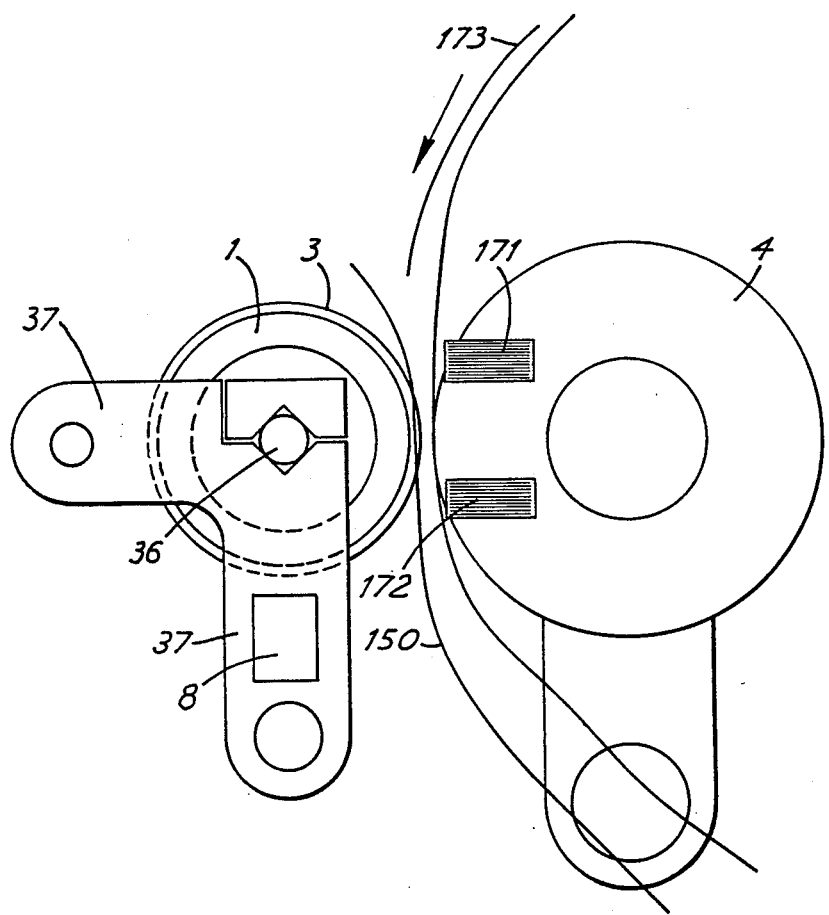
FIG. 13 is a diagrammatic illustration of an alternative construction.
Figure 14:
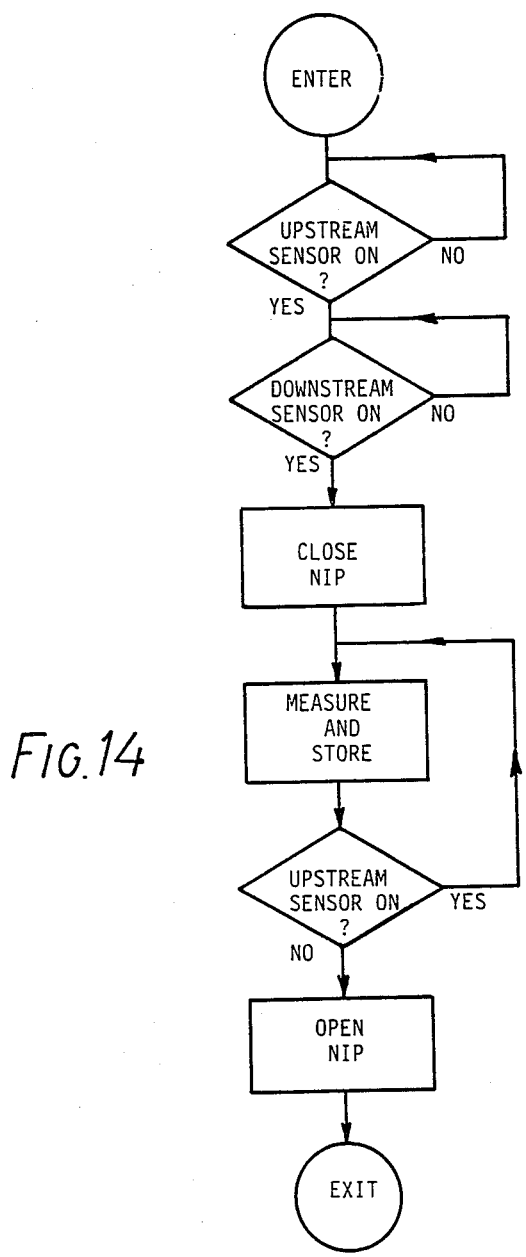
FIG. 14 is a flow diagram of the operation of the apparatus shown in FIG. 13.

In the constructions described above the surface area of paper examined is controlled by the operation of the feed roll 4 but if desired the area examined can be controlled by a predetermined time interval or by using strips of paper of predetermined length and FIG. 13 shows such an arrangement. In the drawing the same reference numerals are used to indicate similar parts but in this arrangement, the combined clutch and brake 27 are replaced by a continuous direct drive, so that the feed roll 4 rotates continuously when the device is in operation. An upstream photoelectric sensor 171 is provided above the nip and a downstream photoelectric sensor 172 below the nip. Control of the device is by a computerised control system the flow diagram for which is shown in FIG. 14. Thus, when the leading edge of a paper strip, indicated by reference numeral 173, enters the nip between the rollers it energises the upstream sensor 171. It then passes through the nip and energises the downstream sensor which causes the pneumatic ram 41 to operate and close the nip. The dust level is then detected by the optic 8 and the measurement stored. When the end of the strip passes the upstream sensor this is signalled to the computer which causes the nip to open thus completing the measurement sequence for that strip.

Figure 15:
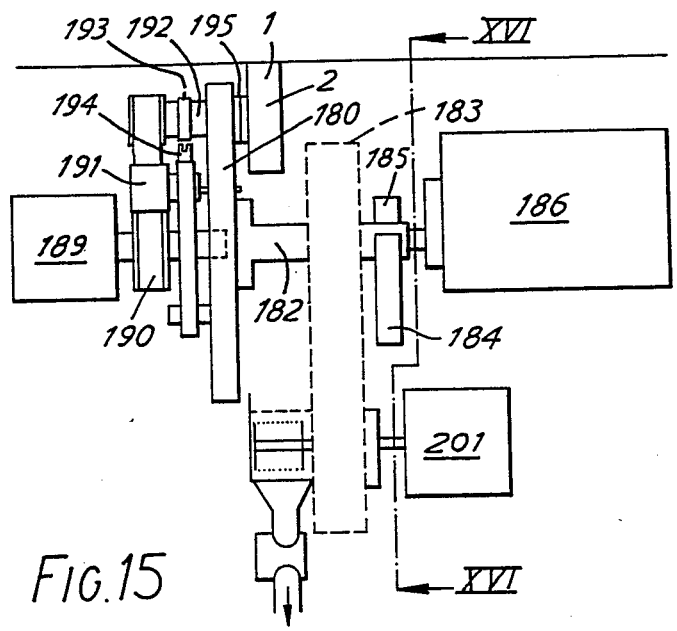
FIG. 15 is a diagrammatic end view of another construction for use with a continuously running sheet of material.
Figure 16:
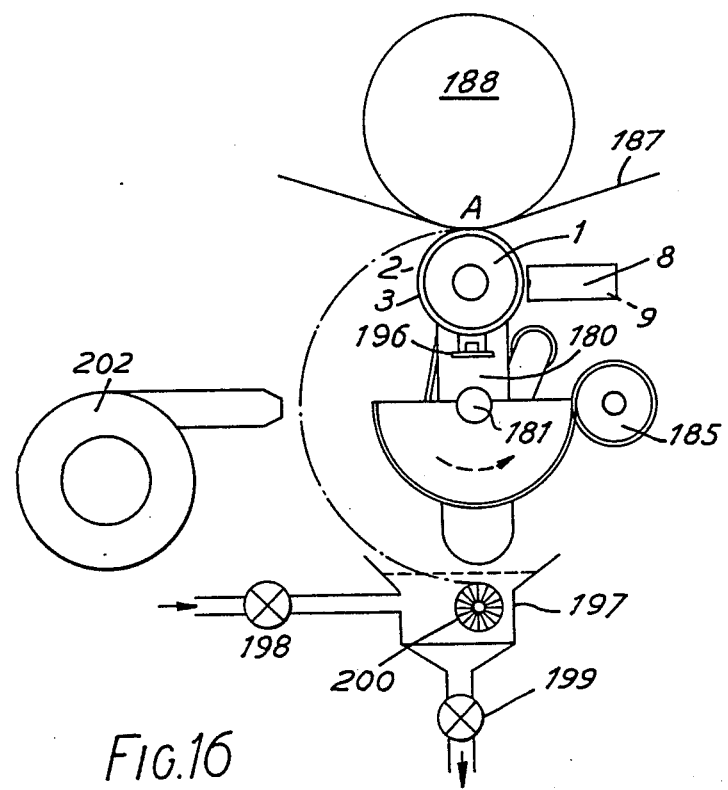
FIG. 16 is a diagrammatic side view on the line XVI—XVI in FIG. 15.
Figure 17:
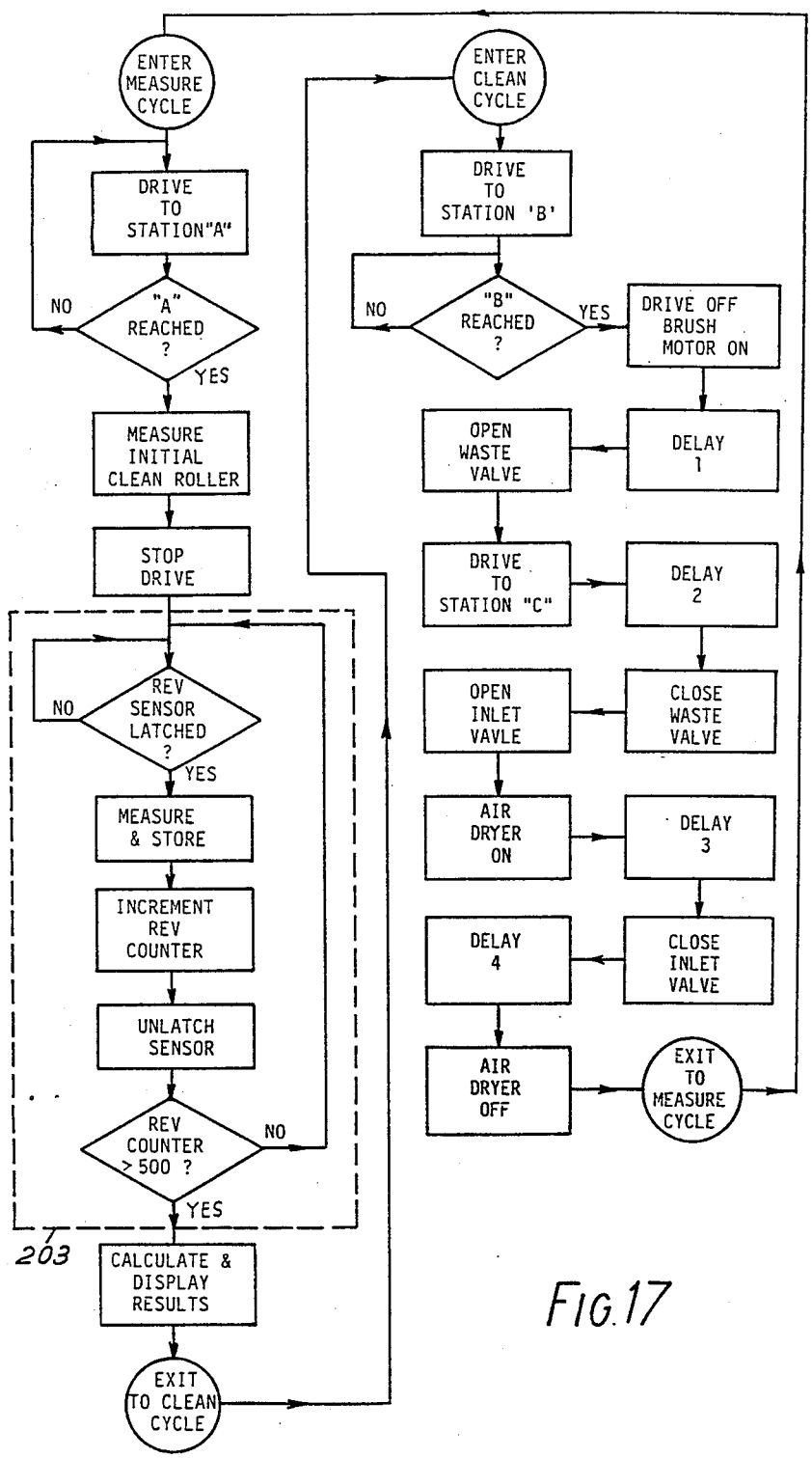
FIG. 17 is a flow diagram of the operation of the apparatus shown in FIGS. 15 and 16.

FIGS. 15, 16 and 17 illustrate means for utilising the invention on a continuously moving sheet and has particular application for determining the propensity of the paper to generate dust when a sheet of paper is being manufactured or coated. A construction for use with a papermaking machine is shown in FIGS. 15 and 16, in which the same reference numerals are used for the parts shown in the previous Figures. As shown in the drawings, the construction comprises a cylindrical roll 1 provided with an elastomeric covering 2 which acts as a reference surface 3. The roll 1 is carried on a pivoted arm 180 which can pivot through 180 degress about a pivot point 181. The arm is carried on a spindle 182 which passes through a mounting 183 and which carries at its other end a toothed quadrant 184. The quadrant meshes with a suitable gear 185 and is driven by a reversible quadrant drive motor 186. Thus, when the quadrant drive motor 186 is actuated the gear 185 drives the quadrant 184 in either direction between positions A and B in FIG. 16 which are disposed 180 degress apart and through an intermediate position C.

The sheet of material to be tested for dust propensity is shown at 187 and is a sheet of paper issuing from the driers of either a papermaking machine or a coating machine. It passes beneath a guide cylinder 188 and the roll 1 closes to provide a nip between itself and this guide cylinder 188 when readings are to be taken. A suitable optic of the kind described with reference to FIGS. 9 and 10 can be used.

The roll 1 is continuously driven from a drive motor 189 through a drive belt 190 at a peripheral speed which is the same as the linear speed of the sheet 187, so that no slip occurs when the roll is brought into contact with the sheet. The belt 190 is tensioned by a jockey pulley 191 mounted on a drive spindle 192 which carries a sensor flag 193. The axis of the drive motor 189 is co-axial with the axis of the drive motor 186. A rotation revolution sensor 194 is provided which co-operates with the flag 193 to record the number of rotations of the roll 1 and a forward slipping clutch indicated by reference numeral 195 is provided between the drive spindle 192 and the roll 1. A pressure adjuster 196 is also included for adjusting the pressure of the roll 1 as it forms the nip with the roll 188.

At position B, that is directly beneath position A, a bath 197 is provided which has an inlet valve 198 and an outlet valve 199 to control the supply of water or cleaning fluid into and out of the bath. A rotatable brush 200 is positioned in the bath 197 and is driven by a brush control motor 201. The brush and bath are located so that when the roll 1 is in position B its surface is contacted by the brush 200.

At the intermediate position C a hot air blower 202 is arranged which can blow hot air onto the roll 1 when it is located at that position.

The apparatus is controlled by a simple computer programme for which the flow diagram is shown in FIG. 17. Thus it will be seen that at the start of the measuring cycle motor 186 is energised to drive the quadrant 184 to position A. The scattered reflectivity of the clean surface of the roll 1 is then initially determined with the optic 8 so as to provide a reference measurement. When the roll reaches the position A, the quadrant drive motor 186 is de-energised and the revolution sensor 194 is simultaneously latched into the system. Continuous measurement of scattered reflectivity is now taken for a predetermined number of revolutions recorded by the increment revolution counter 194, the optic sensor then being unlatched from the system. The results are now calculated in the computer and displayed. The device now enters a cleaning cycle at the start of which the quadrant drive motor 186 is energised to cause the quadrant 184 to rotate to move the roll 1 to position B. When position B has been reached the motor 186 is de-energised and the drive motor 201 for the brush 200 energised. As the roller 1 is still rotating, cleaning takes place. The waste valve 199 is now opened and the quadrant motor is then again energised to move the roll 1 to position C. The waste valve 199 is now closed and the inlet valve 198 opened to refill the bath 197. The air dryer 202 is now operated and after a predetermined delay the inlet valve to the bath 197 is closed, the air dryer is switched off and the device is again ready for use and subsequent movement of the roller 1 to position A. In the delays shown in the flow diagram numbered 1, 2, 3 and 4 typical time periods can be delay 1–480 second, delay 2–20 seconds, delay 3–60 seconds, delay 4–300 seconds.

The switching sequence indicated in broken lines 203 in FIG. 17 occurs once during each rotation of the roller 1 so that incremental build up of scattered reflectance can be determined during the total number of revolutions over which measurement is effected. When the total number of revolutions have been completed, the sensor 89 is unlatched and the sequence proceeds to the washing cycle as described above.

We claim:

1. A method of testing the propensity of a paper or board to dust which comprises passing the paper or board through a nip formed between a reference surface and a feed system, supplementally pressing the reference surface to the surface to be tested at a predetermined pressure and measuring the dust adhering to the reference surface to obtain an indicative reading.

2. A method as claimed in claim 1 which includes measuring the scattered reflectance of the reference surface.

3. A method as claimed in claim 2 which includes measuring the scattered reflectance of the reference surface before pressing said reference surface to the surface to be tested and obtaining an indicative reading by comparing the two measurements.

4. Apparatus for determining the propensity of a paper or board to dust comprising means for passing the paper or board through a nip formed between a reference surface and a feed system, means for supplementally pressing the reference surface to the surface to be tested at a predetermined pressure and means for obtaining an indicative reading from the dust adhering to the reference surface.

5. Apparatus as claimed in claim 4 in which the means for obtaining an indicative reading comprise means for measuring the scattered reflectance of the adhesive surface.

6. Apparatus as claimed in claim 5 including means for measuring the scattered reflectance of the reference surface before pressing it to the surface to be tested, and means for comparing the measurement obtained before pressing with the measurement obtained by pressing it to the surface to be tested to provide an indicative reading.

7. Apparatus as claimed in claim 5 in which the scattered reflectance of the reference surface is measured simultaneously with the passage of the surface over the material being measured.

8. Apparatus as claimed in claim 4 in which the reference surface is substantially cylindrical and thus forms a reference surface cylinder and in which control means are provided to cause the reference surface to move over the surface to be measured for a predetermined distance.

9. Apparatus as claimed in claim 8 in which the reference surface is arranged to press against a feed system to form a nip and feed means are provided to guide the paper or board to be measured between the cylinders.

10. Apparatus as claimed in claim 9 including guide means to prevent the paper or board from adhering to the reference surface.

11. Apparatus as claimed in claim 10 in which said guide means include a deflector for guiding the paper or board away from the reference surface after contact.

12. Apparatus as claimed in claim 9 in which the control means includes means for sensing paper or board in the feed means, to activate the reference cylinder and feed system, and to stop them after a predetermined distance of movement.

13. Apparatus as claimed in claim 9 in which said reference surface cylinder is arranged to contact a continuous web of paper for a predetermined time and to then disengage to an inoperative position.

14. Apparatus as claimed in claim 13 including means for washing the reference surface at the inoperative position.

15. Apparatus as claimed in claim 14 including means for drying the reference surface at an intermediate position between the operative and inoperative positions.

16. Apparatus as claimed in claim 13 in which said reference surface cylinder is continuously rotated.

* * * * *